| United States Patent [19] | [11] Patent Number: 5,015,626 |
| Christian et al. | [45] Date of Patent: May 14, 1991 |

[54] PORCINE SOMATOTROPIN TO IMPROVE MEAT QUALITY OF PIGS

[75] Inventors: Lauren L. Christian, Ames, Iowa; Lindy F. Miller, West Terre Haute, Ind.

[73] Assignee: Iowa State University Research Foundation, Inc., Ames, Iowa

[21] Appl. No.: 388,984

[22] Filed: Aug. 2, 1989

[51] Int. Cl.$^5$ ............... A61K 37/02; C07K 7/10
[52] U.S. Cl. ............................. 514/12; 514/21; 514/806
[58] Field of Search ............................. 514/12, 21, 806

[56] References Cited

U.S. PATENT DOCUMENTS

| 4,517,181 | 5/1985 | Ling et al. | 514/12 |
| 4,582,820 | 4/1986 | Teng | 514/12 |
| 4,585,756 | 4/1986 | Brazeau, Jr. et al. | 514/12 |
| 4,610,976 | 9/1986 | Bohlen et al. | 514/12 |
| 4,694,073 | 9/1987 | Bentle et al. | 514/21 |
| 4,818,531 | 4/1989 | Anderson et al. | 514/12 |
| 4,818,769 | 4/1989 | Nunberg et al. | 514/12 |

OTHER PUBLICATIONS

Polypeptide Factors Influencing Muscle Growth, Dayton et al., CA vol. 107, Dec. 7, 1987, 212441x.

*Primary Examiner*—Lester L. Lee
*Attorney, Agent, or Firm*—Zarley, McKee, Thomte, Voorhees, & Sease

[57] ABSTRACT

Muscle quality of pigs normally susceptible to porcine stress syndrome is improved by administering to the pigs in conjunction with their daily feed ration, a small amount of porcine somatotropin.

7 Claims, No Drawings

PORCINE SOMATOTROPIN TO IMPROVE MEAT QUALITY OF PIGS

BACKGROUND OF THE INVENTION

It is known that certain genotypes of swine are more susceptible to porcine stress syndrome than others. In swine breeding, raising and production, problems associated with porcine stress syndrome are a very real concern. The concern is present because swine suffering from porcine stress syndrome do not perform as well from the standpoint of efficiency of weight gain, quality of meat, and of course profitability. There is, therefore, a need and a continuing effort to develop methods of treating animals susceptible to porcine stress syndrome so that these animals can be effectively and profitably raised.

The fact that these animals are normally intended for ultimate slaughter and consumption by humans raises several associated problems. In particular, any drugs used must be demonstrated to be safe and efficacious and to have no ultimate impact on the general edible quality of the animal's meat. This, of course, eliminates some drug treatments which could otherwise be used with swine to treat porcine stress syndrome. Also, it is very important from the standpoint of consumer acceptability of the meat product that any treatment for porcine stress syndrome not effect the muscle quality of the animal's meat. In particular, swine suffering from porcine stress syndrome often have pale, soft and exudative meat. Of course, if the meat or muscle is pale in color, soft, spongy and exudative, regardless of taste and flavor, it will not be accepted and purchased by consumers.

There is, therefore, a real and continuing need for a way to treat certain genotypes of swine normally susceptible to porcine stress syndrome such that muscle quality problems of the animal often associated with porcine stress syndrome are alleviated.

There is also a continuing need for such a treatment as mentioned above, which in no way adds adulterating drug levels to the meat. Further, there is a continuing need for a way of treatment of genotypes of swine normally susceptible to porcine stress syndrome so that the meat of the animals will not be pale, soft and exudative.

Accordingly, it is a primary objective of the present invention to provide a treatment for genotypes of swine normally susceptible to porcine stress syndrome, which alleviates muscles quality problems normally associated with porcine stress syndrome.

Another objective of the invention is to provide a method of treatment which provides no adulterating drug levels in the meat.

A further objective of the present invention is to provide a treatment which when given to genotypes of swine normally susceptible to porcine stress syndrome minimizes the tendency of the muscle to be pale, soft and exudative.

The method and manner of accomplishing each of the above objectives will become apparent from the detailed description of the invention and the examples which follow.

SUMMARY OF THE INVENTION

This invention involves the application of porcine somatotropin to alleviate muscle quality problems associated with porcine stress syndrome. In particular, if genotypes of swine normally susceptible to porcine stress syndrome are administered a small amount of porcine somatotropin during their period of most rapid weight gain the muscle quality is significantly improved, and in particular is equal to the muscle quality of non-stress genotypes. This indicates that the porcine somatotropin treatment ameliorates the negative effect of stress on muscle quality.

DETAILED DESCRIPTION OF THE INVENTION

In accordance with this invention, porcine somatotropin is administered on a daily basis to animals, in conjunction with their intake of their normal feed ration. Porcine somatotropin, or porcine growth hormone (pGH) is a known natural materials, and can be extracted from the animal itself. Alternatively, porcine growth hormone can be prepared by using recombinant DNA technology to prepare recombinantly derived analogs of porcine somatotropin. For examples of techniques of preparing recombinant DNA derived analogs of porcine somatotropin see U.S. Pat. No. 4,766,224 of Rausch, issued Aug. 23, 1988, which is incorporated herein by reference.

In accordance with the process of the present invention, both naturally extracted porcine growth hormone or recombinant DNA technology produced porcine somatotropin may be used in the process of this invention. As a practical matter, recombinant DNA technology produced porcine somatotropin is the most economical, and therefore the preferred source. Briefly, in the process of preparing pGH, by recombinant DNA technology, pGH is cloned onto expression vectors and used to transform *E. coli* host cells. The pGH is then grown in the *E. coli* host cell, and can thereafter be lysed from the cells, separated from the remainder of the cellular material, isolated and segregated for use.

In accordance with this invention, the animals which are normally susceptible to porcine stress syndrome are provided with daily dosages of the pGH during their period of time for critical weight gain, namely from when they are just out from starter pig phase up to slaughter time. Generally this runs from about the weight of 120 pounds, up to a slaughter weight of 240 pounds. Timewise, this generally means from a period of about three months up to about five to six months of age. If the porcine somatotropin is administered earlier in life less dramatic affect is seen. Likewise, if administration begins much later than about 120 pounds, the affect is not as great.

The manner of administering pGH to the animals can be by injectable. The amount of the dosage will vary, generally in the range of from 0.5 mg per day to 10 mg per day, preferably from 2 mg per day to 8 mg per day. Quite satisfactory results are achieved at 4 mg per day.

The pGH is mixed with normal carrier materials, of natural origin and completely non-harmful to the animal. Such carrier materials may include typical animal pharmaceutical carriers such as dextrose, glucose and polyhydric alcohols such as sorbitol and mannitol. The precise carrier material, where one is employed, is not critical and well within the routine skill for selection.

The following examples are offered to further illustrate but not limit the process of the present invention.

EXAMPLES

In the following examples, 48 pigs were selected as animals for testing. The animals were classified according to their stress genotype. The animals were screened by blood typing, CPK testing, and halothone screening. Thereafter, the animals were characterized as either positive for porcine stress syndrome, as carriers, or as negative. After this classification 48 animals were selected for the test and they were evaluated for rate and efficiency of gain, leg soundness, muscle quality and body composition in response to the administration of pGH or porcine somatotropin. The porcine somatotropin used in the testing was obtained from Pitman-Moore of Terre Haute, Ind.

In particular, forty-eight cross-bred pigs (24 barrows, 24 gilts) were allocated to six treatment groups consisting of eight per group. There were 4 barrows and 4 gilts in each group. They were segregated in the following groups, as indicated in Table I below.

TABLE I

| Treatment | Stress-Positive | Stress-Carrier | Stress-Negative |
| --- | --- | --- | --- |
| PST | 8 (nn PST) | 8 (Nn PST) | 8 (NN PST) |
| Placebo | 8 (nn) | 8 (Nn) | 8 (NN) |

As illustrated in Table I, the forty-eight animals were broken into the three genotypes, stress-positive, stress-carriers, and stress-negative. These animals were in groups of eight, with one group being positively treated with porcine somatotropin (PST) and with another like group of eight being treated with placebo. The placebo was a sterile diluent carrier, absent the PST. The pigs were fed an ad libitum corn-soybean diet formulated to contain 17.6% protein and 1.2% lysine. Two pigs of the same sex and stress classification and treatment were housed per pen in a concrete floored confinement building. Assignment to pens occurred prior to 70 pounds of average weight but the pigs were not started on the treatment of the invention until the total pen weight reached 240 pounds indicating the animals' weight average of 120 pounds. These pigs normally were at about 3 months of age at this time.

The pigs began injection with porcine somatotropin at 4 mg per head, or with the placebo at the time the total pen weight of two pigs each reached 240 pounds. The pigs were injected once per day until they were taken off of the test. They were taken off of the test when the weight of each animal reached 240 pounds, which was approximately between five and six months of age.

Backfat measurements at the last rib (1-2 inches off the midline) were taken with a Renco ultrasonic machine and the pigs were scored on soundness at the start and the end of the test. The porcine somatotropin treatments were terminated at weekly intervals as individual pigs reached 240 pounds. The animals were then fed for six additional days before slaughter. Forty-five minutes after slaughter longissimus muscle samples were collected for determination of muscle pH. Standard carcass measurements were made from 24 hours chilled carcasses and the tenth and eleventh rib longissimus muscle sample was collected and utilized for determining muscle quality (color, texture, marbling), muscle reflectance and percent transmittance of light. Muscle reflectance is determined by placing a light reflecting meter on the top of a porcine muscle and taking a reading. The percent of transmittance is measured by the percent of transmission of light through the muscle. Generally, the higher the transmission number the less desirable the meat quality because it is more pale in color and more watery. Likewise, the higher the reflectance the less desirable because the meat is paler in color. With regard to pH change, the higher the pH the greater the water-holding capacity of the meat which is of economic importance in the processing of the meat.

Table II shows the mean scores for each of the eight animals in the groups.

TABLE II

| | Test Results | | | | | |
| --- | --- | --- | --- | --- | --- | --- |
| Measurement | NN (N = 8) | NNPST (n = 8) | Nn (n = 8) | NnPST (n = 8) | nn (n = 8) | nnPST (n = 7) |
| 45 Min., pH | 6.5 | 6.5 | 6.3 | 6.1 | 5.6 | 5.9 |
| Reflectance | 25.1 | 21.1 | 27.5 | 23.9 | 30.5 | 25.4 |
| % Transmission | 24.4 | 12.4 | 26.1 | 24.8 | 83.9 | 50.8 |
| 24 Hr. pH | 5.5 | 5.7 | 5.5 | 5.5 | 5.4 | 5.5 |

As can be seen, the average 45 minute muscle pH was similar for both treated and control animals with the NN and Nn genotypes, but a positive effect of porcine somatotropin on the nn animals was noted. The ultimate pH of the NNPST was higher, and differences for nnPST were observed. Muscle color approached normal, and transmittance was lower for nn than NN. Reflectance values were reduced for NNPST and nnPST groups compared with their respective controls. In other tests lower marbling scores tend to occur in the treated negative genotypes and lean texture of the loin muscle improved in nnPST versus nn. In general, it can be seen from the table that administration of porcine somatotropin during the critical growth months improved both quality and qualitative carcass characteristics of all genotypes.

What is claimed is:

1. A method of improving muscle quality of pigs normally susceptible to procine stress syndrome, said method comprising: administering daily to said pigs during their period of time for critical weight gain, in conjunction with their daily feed ration a small but muscle quality improving effective amount of procine somatotropin.

2. The method of claim 1 wherein said administration occurs from the live weight of about 120 pounds to a live weight of about 240 pounds.

3. The method of claim 1 wherein the porcine somatotropin is a recombinant DNA produced porcine somatotropin.

4. The method of claim 1 wherein the administration is by injection.

5. The method of claim 1 wherein the administration is by intramuscular injection.

6. The method of claim 1 wherein the dosage level is from 0.5 mg per day to about 10 mg per day.

7. The method of claim 6 wherein the dosage level is from about 2 mg per day to about 8 mg per day.

* * * * *